United States Patent [19]
Shoesmith, deceased et al.
[11] Patent Number: Plant 6,837
[45] Date of Patent: Jun. 6, 1989

[54] CHRYSANTHEMUM PLANT NAMED PEKOE

[75] Inventors: Leonard H. Shoesmith, deceased, late of Westfield, United Kingdom, by May Victoria Shoesmith, executrix; Peter S. Hesse, Brandenton, Fla.

[73] Assignee: Ball Seed Company, Chicago, Ill.

[21] Appl. No.: 150,066

[22] Filed: Jan. 29, 1988

[51] Int. Cl.[4] ..... A01H 5/00
[52] U.S. Cl. ..... Plt./74
[58] Field of Search ..... Plt./74

*Primary Examiner*—Robert E. Bagwill
*Attorney, Agent, or Firm*—Foley & Lardner, Schwartz, Jeffery, Schwaab, Mack, Blumenthal & Evans

[57] ABSTRACT

A Chrysanthemum plant named Pekoe having orange-bronze anemone flowers, dark orange-bronze mature disc florets, eight week flowering response; compact, freely branching growth habit, prolific blooming habit, and excellent keeping quality.

1 Drawing Sheet

The present invention comprises a new and distinct cultivar of *Dendranthema grandiflora,* hereinafter referred to by the cultivar named Pekoe.

Pekoe is a product of a planned breeding program which had the objective of creating new Chrysanthemum cultivars with early flower response, anemone flower form, and compact habit, making it suitable for pot mum programs. Such traits in combination were not present or needed improvement in previously available commercial cultivars.

Pekoe was originated from a hybridization made in a controlled breeding program in Westfield-Woking, England by Leonard H. Shoesmith in 1980. The male and female parents are unknown. Pekoe was discovered and selected as one flowering plant within the progeny of the stated cross by Peter S. Hesse in November, 1981 in a controlled environment in Parrish, Fla.

The first act of asexual reproduction of Pekoe was accomplished when vegetative cuttings were taken from the initial selection in February, 1982 in a controlled environment in Parrish, Fla. by a technician working under formulations established and supervised by Peter S. Hesse. Horticultural examination of selected units initiated in October, 1982 has demonstrated that the combination of characteristics as herein disclosed for Pekoe are firmly fixed and are retained through successive generations of asexual reproduction.

Pekoe has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Pekoe, which in combination distinguish this Chrysanthemum as a new and distinct cultivar:

1. Orange-bronze anemone flowers; ray florets curl inward near base shown in a lighter color underside.
2. Mature disc florets are dark orange-bronze and the petal margins at the apex are golden bronze.
3. Immature (prior to opening) disc florets are yellow-green.
4. Eight week flower response.
5. Compact, freely branching growth habit.

6. Prolific bloomer.
7. Excellent keeping quality.

Of the many commercial cultivars known to the present inventors, the most similar in comparison to Pekoe is Rave, disclosed in U.S. Plant Pat. No. 5,738. Reference is made to Chart A which compares certain characteristics of Pekoe to those same characteristics of Rave. In comparison to Rave, Pekoe has bronze flower color, smaller flowers, and a more compact habit. The eight week flower response and anemone flower form are similar to those same characteristics of Rave.

The accompanying photographic drawing shows typical inflorescence and foliage characteristics of Pekoe, with colors being as nearly true as possible with illustrations of this type. The photograph is in black and white with a few flowers being in color to accurately depict ray and disc floret color.

In the following description, color references are made to The Royal Horticultural Society Colour Chart. The color values were determined between 2:40 and 2:50 p.m. on Jan. 1, 1988 under fluorescent lighting at Parrish, Fla.

Classification:
*Botanical.*—*Dendranthema grandiflora,* cv. Pekoe.
*Commercial.*—Anemone pot.

INFLORESCENCE

A. Capitulum:
*Form.*—Flat.
*Type.*—Anemone.
*Diameter across face.*—5–6.5 cm.

B. Corolla of ray florets:
*Color (general tonality from a distance of three meters).*—Orange-bronze.
*Color (upper surface).*—168B fading to 168D.
*Color (under surface).*—168C.

C. Corolla of disc florets:
*Color (mature).*—168A, apex tipped with gold.
*Color (immature).*—142B.

D. Reproductive organs:
*Androecium.*—Present in disc florets only.
*Gynoecium.*—Present in both disc and ray florets.

PLANT

A. General appearance:

*Height.*—22 cm when grown pinched in a 6½" pot. Height can vary depending upon growing conditions.

B. Foliage:

*Color (upper surface).*—147A.

*Color (under surface).*—147B.

*Shape.*—Ovate, deeply lobed and crenate.

CHART A

| | Pekoe | Rave |
|---|---|---|
| General tonality | Orange-bronze | lavender-pink |

-continued

CHART A

| | Pekoe | Rave |
|---|---|---|
| Flower diameter | 5–6.5 cm | 6–7 cm |
| Flower response | 8 weeks | 8 weeks |
| Average number of ray florets | 38 | 32 |
| Disc diameter | 22–26 mm | 25–32 mm |
| Disc floret length | 8–12 mm | 10–15 mm |
| Ray floret length | 20–30 mm | 25–32 mm |
| Ray floret width | 5–8 mm | 8–11 mm |

It is claimed:

1. A new and distinct cultivar of Chrysanthemum plant named Pekoe, as illustrated and described, and parts thereof.

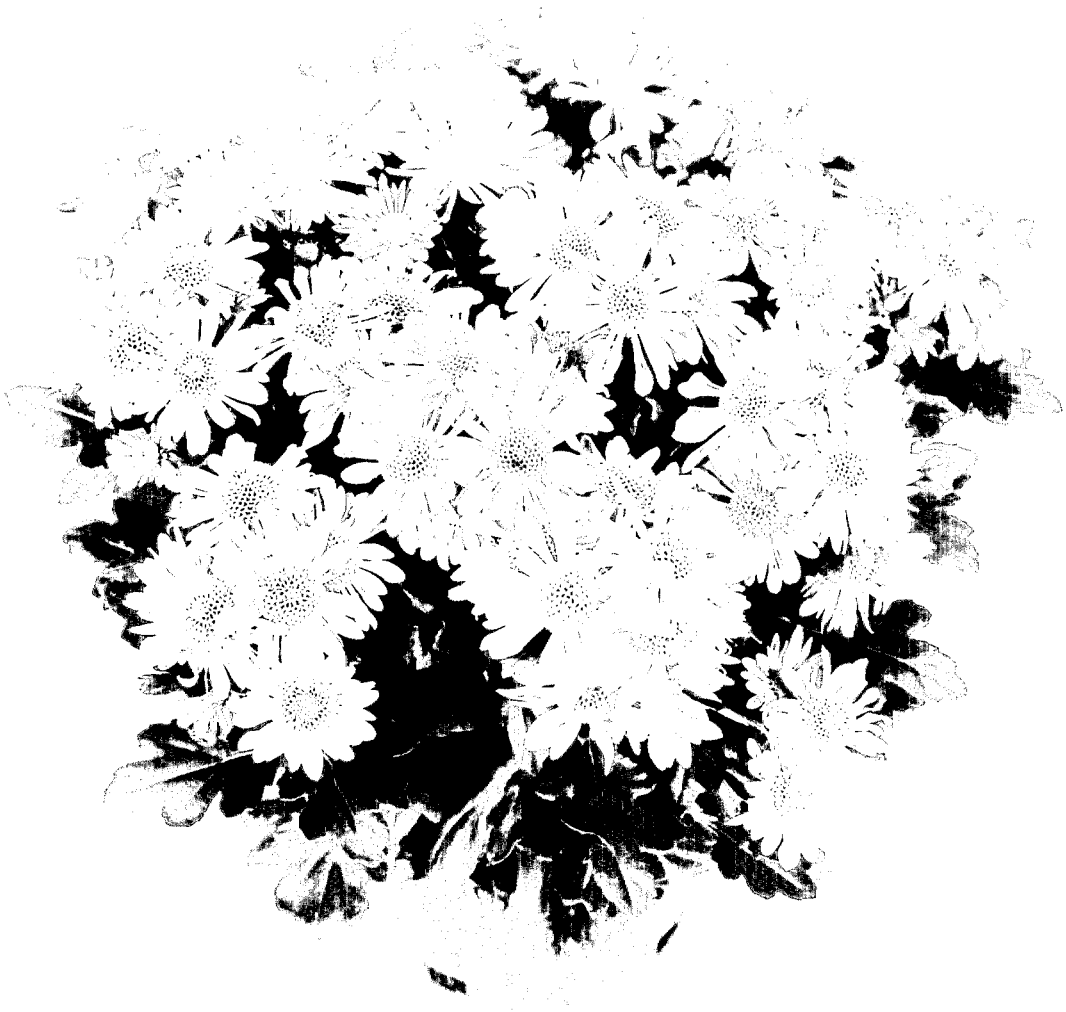

* * * * *